United States Patent
Callahan et al.

(10) Patent No.: US 11,940,387 B2
(45) Date of Patent: Mar. 26, 2024

(54) PORTABLE LIQUID ANALYZER

(71) Applicant: Veriteque USA, Inc., Carson City, NV (US)

(72) Inventors: Michael D. Callahan, Glenwood Springs, CO (US); Christian Loane, Blackheath (AU)

(73) Assignee: Veriteque USA, Inc., Carson City, NV (US)

( * ) Notice: Subject to any disclaimer, the term of this patent is extended or adjusted under 35 U.S.C. 154(b) by 616 days.

(21) Appl. No.: 16/989,449

(22) Filed: Aug. 10, 2020

(65) Prior Publication Data

US 2020/0371038 A1    Nov. 26, 2020

Related U.S. Application Data

(60) Continuation of application No. 15/982,050, filed on May 17, 2018, now Pat. No. 10,942,126, which is a division of application No. 14/856,671, filed on Sep. 17, 2015, now Pat. No. 9,989,473.

(51) Int. Cl.
   *G01N 33/22* (2006.01)
   *G01N 21/78* (2006.01)
   *G01N 31/22* (2006.01)

(52) U.S. Cl.
   CPC .............. *G01N 21/78* (2013.01); *G01N 31/22* (2013.01); *G01N 33/227* (2013.01)

(58) Field of Classification Search
   CPC ....... G01N 21/78; G01N 31/22; G01N 33/227
   See application file for complete search history.

(56) References Cited

U.S. PATENT DOCUMENTS

| | | | |
|---|---|---|---|
| 3,528,780 A | | 9/1970 | Radawski |
| 3,925,018 A | * | 12/1975 | Saunders ............... G01N 21/78 |
| | | | 435/7.1 |
| 4,788,039 A | | 11/1988 | Glattstein |
| 5,296,380 A | | 3/1994 | Margalit |
| 5,332,662 A | | 7/1994 | Ullman |
| 5,480,612 A | | 1/1996 | Margalit |
| 5,550,061 A | * | 8/1996 | Stone ..................... G01N 21/78 |
| | | | 436/83 |
| 5,648,047 A | | 7/1997 | Kardish et al. |
| 8,647,451 B2 | | 2/2014 | Apblett et al. |
| 9,989,473 B2 | | 6/2018 | Callahan |
| 10,330,603 B1 | | 6/2019 | Callahan |
| 10,942,126 B2 | | 3/2021 | Callahan et al. |
| 2002/0173047 A1 | * | 11/2002 | Hudak .................. B01L 3/5023 |
| | | | 436/178 |
| 2009/0029480 A1 | | 1/2009 | Loane |
| 2009/0068065 A1 | | 3/2009 | Pagoria et al. |
| 2014/0017802 A1 | | 1/2014 | Smith |
| 2014/0127824 A1 | | 5/2014 | Amisar |

(Continued)

FOREIGN PATENT DOCUMENTS

WO    WO-2005059162 A2 *    6/2005    ............... C12Q 1/04

*Primary Examiner* — Brian J. Sines
(74) *Attorney, Agent, or Firm* — Gavrilovich, Dodd & Lindsey LLP

(57) ABSTRACT

A system is provided for identifying the presence of a target molecule or ion. The system comprises a solid support, and at least one chemical reagent applied to the solid support. Each chemical reagent produces a presumptive color indication that identifies or excludes the presence of a target molecule or ion.

9 Claims, 1 Drawing Sheet

(56) References Cited

U.S. PATENT DOCUMENTS

2014/0366796 A1* 12/2014 Cincotta .................. G04F 1/00
  156/60
2015/0185125 A1   7/2015  Danylewych-May
2015/0268215 A1   9/2015  Tomellini et al.
2016/0109371 A1   4/2016  Blair
2019/0353597 A1  11/2019  Callahan et al.

* cited by examiner

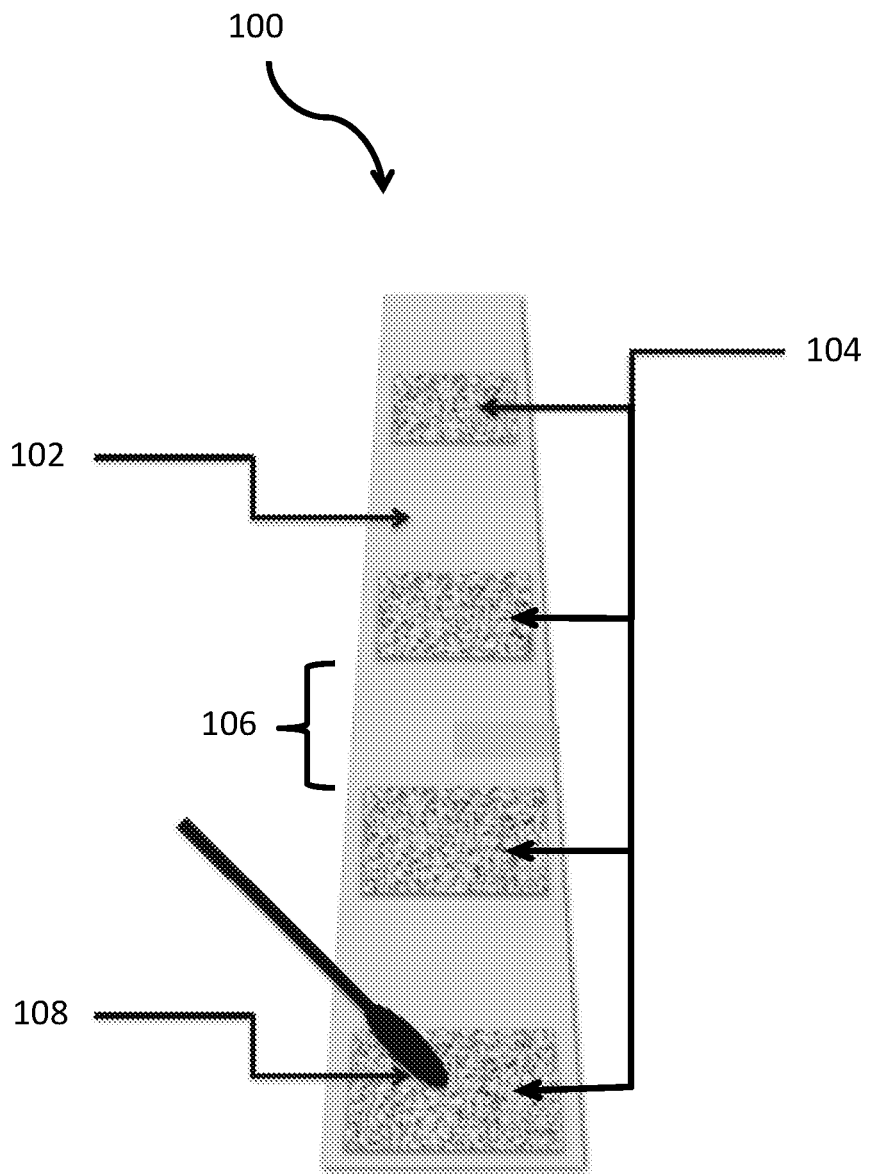

PORTABLE LIQUID ANALYZER

CROSS-REFERENCE TO RELATED APPLICATION

This application is a continuation of and claims the benefit under 35 U.S.C. § 120 to U.S. application Ser. No. 15/982,050 filed May 17, 2018, currently allowed, which is a divisional application of and claims the benefit under 35 U.S.C. § 120 to U.S. application Ser. No. 14/856,671, filed Sep. 17, 2015, and granted as U.S. Pat. No. 9,989,473, the contents of each of which is hereby incorporated by reference in its entirety.

TECHNICAL FIELD

The present invention relates to a system capable of identifying the presence of target molecule(s) and ion(s), a method for preparing a system capable of identifying the presence of target molecule(s) and ion(s), and a method for performing a test for the presence of target molecule(s) and ion(s).

BACKGROUND ART

Liquid borne energetic devices are a significant threat to the global mass transit industry. All transit sectors including Air, Land, Sea and border control check points remain at constant high threat alert levels. Mass transit and mass screening requires cost effective, rapid and reliable technology designed for presumptive identification of concealable threat liquid materials.

A variety of threat energetic liquid testing devices are commercially available. By way of example to illustrate the following section some commercially available kits include, but are not limited to: Hach Hydrogen Peroxide Test Kit, Model HYP-1, EM Quant® Peroxide Test, Catalog No. 10011, Gillardoni FEP ME 640 AMX X-ray, ChemSee Portable explosive test kit, Field forensics ELITE™ System, FIDO X3 Explosive detector, TraceX Explosive Kit. Broadly these devices can be divided into two groups: (i) electronic and (ii) non-electronic. Electronic devices are high cost and although some offer portability, most are laboratory bench mounted systems. (ii) Non-electronic devices are lower cost single use devices, adapted for ease in portability, offering presumptive identification of known energetic liquids.

Non-electronic devices can further be divided into two broad groups: (a) competitive immuno-assay based devices and (b) "spot test" devices which are composed of chemical reagents that react with chemical an analyte compound to give a known presumptive color indication.

Prior art commercially available spot test devices all suffer from a combination of issues which may include, but are not limited to: (i) devices are only designed to presumptively identify a single threat energetic liquid. In order to identify several threat energetic liquids, many different test devices would be required, perhaps from several different manufacturers; (ii) to facilitate a presumptive chemical reaction, commercially available devices may comprise hazardous acidic or alkaline liquid reagents; (iii) to facilitate a presumptive chemical reaction, commercially available devices may comprise volatile liquid organic solvents; (iv) the packaging required for most devices comprises a combination of glass ampoules which must be broken, reinforced heavy duty plastic baggies for storage of used hazardous chemical reagent(s), pressurized spray cans containing aerosolized hazardous chemical reagents, screw top reaction vessels, and batteries to power reaction devices or electronic eye color development systems; (v) virtually all commercially available devices require multi-step reaction sequences in order for a single unknown analyte to be tested. In summary, all commercially available devices are costly, require excessive equipment and packaging, comprise hazardous liquids exposure operators to unnecessary OHS risks, do not meet air shipping requirements, and require excessive analytical time.

SUMMARY OF THE INVENTION

The present invention provides a system for identifying the presence of a target molecule or ion. The system comprises a solid support, and at least one chemical reagent applied to the solid support. Each chemical reagent produces a presumptive color indication that identifies or excludes the presence of a target molecule or ion.

The present invention also provides a method for producing a test kit to identify the presence of a target molecule or ion. The method comprises providing a solid support, and applying a first chemical reagent to the solid support, the first chemical reagent producing a presumptive color indication that identifies or excludes the presence of a first target molecule or ion.

The present invention further provides a method for identifying the presence of a target molecule or ion. The method comprises transferring a molecule or ion from a surface to a first chemical reagent applied to a solid support, and allowing the chemical reagent to react with the transferred molecule or ion, whereby a presumptive color indication is produced that identifies or excludes the presence of the transferred molecule or ion as a first target molecule or ion.

BRIEF DESCRIPTION OF THE DRAWING

The FIGURE is a top view of an embodiment of a device of the present invention that is capable of identifying the presence of target molecule(s) and ion(s).

DETAILED DESCRIPTION OF THE PREFERRED EMBODIMENT

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Referring to the FIGURE, embodiments of a system 100 of the present invention are capable of identifying the presence of target molecule(s) and ion(s). The system 100 may be provided in the form of a solid support 102 coated with one or more dry chemical reagents 104, upon which the analysis of target molecule(s) and ion(s) is performed and upon which a presumptive color indication can develop. The solid support 102 may be provided in the form of glass, metal, paper, textiles, organic and inorganic membranes. The individual dry coated chemical reagent(s) 104 may be spaced apart from one another by a physical gap 106 on the solid support 102 to prevent contamination and maintain selectivity and reactivity for target molecule(s) and ion(s).

The system 100 of the present invention may comprise a means for introducing target molecule(s) and ion(s) to at least one chemical reagent 104 that can provide a presumptive color indication in the presence of target molecule(s) and ion(s). The means for introducing the target molecule(s) and ion(s) to at least one chemical reagent is provided in the form of a swab 108. The swab 108 may be composed of any material that will assist in the transfer of the target molecule(s) and ion(s) to the chemical reagent(s) 102. Preferably the swab 108 is dry and comprises an unreactive, adsorbent material such as cotton. The system 100 of the present invention may be stored in a moisture and UV resistant package prior to use, such as PET12um/AL7um/PE50.

The presumptive color indication that is developed after each target molecule is applied to a chemical reagent 102 may be observed in any part of the electromagnetic spectrum, preferably in the visible spectrum.

The system 100 of the present invention may be used for identifying all classes of energetic liquid(s) molecule(s) and ion(s) and energetic liquid precursor(s) molecule(s) and ion(s). The energetic liquid(s) and ion(s) and energetic liquid precursor(s) may comprise chemico-physical properties or be selected from a group including, but not limited to, dissolved hydrogen ion activity, organic solvents, liquids comprising reactive nitrogen, oxygen, halogen(s) or free radical(s).

Where the target molecule(s) and ion(s) is dissolved hydrogen ion activity the chemical reagent(s) 104 may preferably be selected from the group comprising cresol red, methyl violet, crystal violet, ethyl violet, malachite green, methyl green, 2-(p-dimethylaminophenylazo)pyridine, paramethyl red, metanil yellow, 4-phenylazodiphenylamine, thymol blue, metacresol purple, orange IV, 4-o-tolylazo-o-toluidine, quinaldine red, 4,4'-bis(4-amino-1-naphthylazo)-2,2'-stilbenedisulfonic acid, p-naphtholbenzein, phenolphthalein, o-cresolphthalein, ethyl bis(2,4-dimethylphenyl) ethanoate, Thymolphthalein, alizarin yellow R, alizarin, p-(2,4-dihydroxyphenylazo) benzenesulfonic acid, sodium salt, 5,5'-indigodisulfonic acid, disodium salt, 2,4,6-trinitrotoluene, 1,3,5-trinitrobenzene, clayton yellow. The reagent 104 preferably comprises about 0.1-0.2% w/w of the system 100.

Where the target molecule(s) and ion(s) is an organic solvent(s) the chemical reagent(s) 104 may preferably be selected from the group comprising merocyanine dyes, 4-[2-N-substituted-1,4-hydropyridin-4-ylidine)ethylidene] cyclohexa-2,5-di-en-1-one, red pyrazolone dyes, azomethine dyes, indoaniline dyes, diazamerocyanine dyes, indigoid dyes 2,6-diphenyl-4-(2,4,6-triphenylpyridinium-1-yl)phenolate, 1-ethyl-4-(methoxycarbonyl)pyridinium iodide, 5-(dimethylamino)-5'-nitro-2,2'-bisthiophene, reichart's dye, (2,4,6-triphenyl-1-pyridinio)-2,6-diphenylphenolate, 9-diethylamino-5-benzo[α]phenoxazinone. The reagent preferably 104 comprises about 0.1-0.2% w/w of the system 100.

Where the target molecule(s) and ion(s) is reactive nitrogen the chemical reagent(s) 104 may preferably be selected from the group comprising 6-amino-1-naphthol-3-sulphonic acid, zinc, diphenylbenzidine, phenylanthranilic acid, aniline sulfate, diphenylamine, ethylenediamine, N-1 naphthyl dihydrochloride, potassium iodide, bismuth nitrate, sulfamic acid, sodium hydrogen sulphate, sulfanilamide, hexachloroplatinic(IV) acid hydrate. The reagent 104 preferably comprises about 0.1-0.2% w/w of the system 100.

Where the target molecule(s) and ion(s) is reactive oxygen, halogen(s) or free radical(s)s the chemical reagent(s) 104 may preferably be selected from the group comprising ammonium thiocyanate, 2,2'-bipyridine (Ru complex), nitrophenanthroline (Fe complex), manganous sulphate, phenylanthranilic acid, 1,10-phenanthroline iron(II) sulfate complex, indigo carmine, copper sulphate, N-ethoxychrysoidine, analine, 2,2'-Bipyridine (Fe complex), methylene blue, 5,6-dimethylphenanthroline (Fe complex), o-dianisidine, ferrous sulphate, p-amino-N,N-diethylaniline sulfate, Sodium diphenylamine sulfonate, diphenylbenzidine, diphenylamine, viologen. The reagent 104 preferably comprises about 0.1-0.2% w/w of the system 100.

In accordance with the present invention, there is also provided a method for preparing a system 100 capable of identifying all classes of energetic liquid(s) molecule(s) and ion(s) and energetic liquid precursor(s) molecule(s) and ion(s). The system 100 comprises at least one chemical reagent 104 which can provide a presumptive color indication in the presence of target molecule(s) and ion(s), wherein a single chemical reagent 104 or a mixture of chemical reagents 104, purchased in micronized powder form or milled to correct mesh size, are provided in micronized powder form to a dispersant media, mixed by rapid agitation forming a temporary liquid dispersion.

Preferably the method comprises the further step of introducing the temporary homogenized liquid dispersion of a micronized powder of chemical reagent 104 or a mixture of chemical reagents 104 and dispersant to a solid support article 102, applying a known quantity of dispersion to the solid support article 102 by a suitable method chosen from the group including, but not limited to, letterpress, rotary gravure, screen printing, tampography, wax printing, contact dosing, ultrasonic sputter and drop on demand printing.

Preferably the method comprises the further step of removing the dispersion coated solid support article 102 for drying, which may be done by hot air evaporation.

In one form of the invention, the system 100 may comprise only one dried chemical reagent dispersion 104 or dried chemical reagent mix dispersion 104 applied to the solid support surface 102 and dried, which provides a single identification for one class of target energetic liquid(s) molecule(s) and ion(s) and energetic liquid precursor(s) molecule(s) and ion(s) in a single test.

Preferably the system 100 will comprise several individual dried chemical reagent(s) dispersion 104 or dried chemical reagent mix dispersion(s) 104 applied to the solid support surface 102, which provides identification for all classes of target energetic liquid(s) molecule(s) and ion(s) and energetic liquid precursor(s) molecule(s) and ion(s) in a single test.

Preferably multiple applications of chemical reagent dispersion(s) 104 or chemical reagent mix dispersion(s) 104 will be physically separated from one another by a void or gap 106 between the boundary edge of one applied dried chemical reagent(s) dispersion 104 or dried chemical reagent mix dispersion(s) 104 and another on the solid support surface 102. Preferably the physical void or separation 106 is a minimum of about 1 mm.

In accordance with the current invention, the method may comprise the further step of guillotine or stamp cutting or shaping the solid support surface 102 into a final design. The solid support 102 composition and dimensions and shape of the final device design are limited only by end user requirements.

In accordance with the current invention, a method for packaging comprises hermetically sealing the device inside a moisture and UV protective packet composed of, for example, PET12um/AL7um/PE50.

In accordance with the present invention, there is provided a method for using a system 100 capable of identifying all classes of target energetic liquid(s) molecule(s) and ion(s) and energetic liquid precursor(s) molecule(s) and ion(s). The method comprises the transfer of target molecule(s) and ion(s) from a surface or container to the surface of the system 100, rubbing the target molecule(s) and ion(s) into applied dried chemical reagent(s) dispersion 104 or dried chemical reagent mix dispersion(s) 104, thereby mixing the energetic liquid(s) molecule(s) and ion(s) and energetic liquid precursor(s) molecule(s) and ion(s) with the applied dried chemical reagent(s) dispersion 104 or dried chemical reagent mix dispersion(s) 104. The target energetic liquid(s) molecule(s) and ion(s) and energetic liquid precursor(s) molecule(s) and ion(s) may be identified by the development of presumptive color(s) on the device solid support surface 104.

Preferably, the step of rubbing the transferred target energetic liquid(s) molecule(s) and ion(s) and energetic liquid precursor(s) molecule(s) and ion(s) into multiple applied dried chemical reagent(s) dispersion 104 or dried chemical reagent mix dispersion(s) 104 would be done successively to one applied dried chemical reagent(s) dispersion 104 or dried chemical reagent mix dispersion(s) 104 after another. Such a process facilitates the identification of all classes of target energetic liquid(s) molecule(s) and ion(s) and energetic liquid precursor(s) molecule(s) and ion(s) in a single test.

Preferably, the step of transferring the target energetic liquid(s) molecule(s) and ion(s) and energetic liquid precursor(s) molecule(s) and ion(s) from a surface or container to the surface of the system 100 comprises rubbing or dipping a swab tip 108 onto a surface or into a container containing a liquid, thereby absorbing a suitable volume or portion of the liquid from the surface or container into the swab tip matrix, and then rubbing the swab tip onto the surface of the system 100, thereby completing the transfer of the target energetic liquid(s) molecule(s) and ion(s) and energetic liquid precursor(s) molecule(s) and ion(s) onto the system 100.

Advantageously, the method and system 100 of the present invention reduces the cost of manufacturing a device capable of identifying all classes of energetic liquid(s) molecule(s) and ion(s) and energetic liquid precursor(s) molecule(s) and ion(s) in a single test, minimizes wastage during manufacture and post usage of such devices, greatly reduces the time necessary to perform a test, thereby reduces the use of and exposure to hazardous reagents to end users and the environment. Further the system 100 of the present invention is robust, easily transportable, and simple to use by untrained personnel.

The chemical reagent(s) 104 may be purchased in micronized powders and added to the dispersant. Rapid agitation is applied to produce an homogenized flowable liquid dispersion.

The system 100 of the present invention may comprise as many chemical reagent(s) or chemical reagent 104 mixes applied to the solid support 102 as is necessary to identify all target energetic liquid(s) molecule(s) and ion(s) and energetic liquid precursor(s) molecule(s) and ion(s). As the range of target liquids expands with time, the chemical reagent(s) 104 or chemical reagent mixes 104 applied to the solid support 102 will also expand and will continue to include a dry non-reactive absorbent swab 108 for sample collection and transfer. The system 100 may be packaged in a PET12um/AL7um/PE50 moisture and UV resistant material.

Examples of the preparation of reagents for the system 100 for the detection of various target molecules include the following. It will be appreciated that other methods of preparation may be employed and that other molecules may be targeted.

Hydrogen Ion Activity—Device Preparation 1-2% w/w malachite green, 5-10% w/w polyvinylpyrrolidone, 2-5% w/w isopropyl alcohol, 83-92% water are added together, homogenized for 20 minutes into a dispersion and applied by drop on demand printing onto the paper surface and hot blown air dried. The paper is guillotined into a suitable device shape and hermetically sealed into a PET12um/AL7um/PE50 sachet. The system 100 is supplied with a hermetically sealed dry cotton tipped swab 108.

Organic Solvent—Device Preparation 1-2% w/w Reichardt's dye, 5-10% w/w methylcellulose, 2-5% w/w isopropyl alcohol, 83-92% water are added together, homogenized for 20 minutes into a dispersion and applied by drop on demand printing onto the paper surface and hot blown air dried. The paper is guillotined into suitable device shape and hermetically sealed into PET12um/AL7um/PE50 sachet. The system 100 is supplied with a hermetically sealed dry cotton tipped swab 108.

Reactive Nitrogen—Device Preparation 1-2% w/w bismuth nitrate, 5-10% w/w sodium hydrogen sulphate, 5-10% w/w potassium iodide, 68-89% water are added together, homogenized for 20 minutes into a dispersion and applied by rotary gravure printing onto the paper surface and hot blown air dried. The paper is guillotined into a suitable device shape and hermetically sealed into PET12um/AL7um/PE50 sachet. The system 100 is supplied with a hermetically sealed dry cotton tipped swab 108.

Reactive Oxygen, Halogen or Free Radical—Device Preparation 1-5% w/w ferrous sulphate, 1-3% w/w sodium hydroxide, 10-15% w/w isopropyl alcohol, 60-70% w/w water, 5-10% w/w polyvinylpyrrolidone are added together, homogenized for 20 minutes into a dispersion and applied by silk screen printing onto the paper surface and hot blown air dried. The paper is guillotined into a suitable device shape and hermetically sealed into PET12um/AL7um/PE50 sachet. The system 100 is supplied with a hermetically sealed dry cotton tipped swab 108.

Embodiments of the present invention are adapted to detect the presence of energetic liquid(s) molecule(s) and ion(s) and energetic liquid precursor(s) molecule(s) and ion(s) and does not require multiple steps to carry out a single test.

The system of the present invention is capable of identifying all classes of energetic liquid(s) molecule(s) and ion(s) and energetic liquid precursor(s) molecule(s) and ion(s). The system comprises at least one chemical reagent which can provide a presumptive color indication in the presence of target molecule(s) and ion(s).

The system of the present invention is adapted to identifying the presence of all classes of target energetic liquid(s) molecule(s) and ion(s) and energetic liquid precursor(s) molecule(s) and ion(s) in a single test. The system does not include glass packaging which is manually broken, hazardous liquid or aerosolized chemical reagents, or electronic components.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed:

1. A method for identifying the presence of a target molecule or ion, comprising:
    transferring a molecule or ion from a surface to a first chemical reagent applied to a solid support; and
    allowing the chemical reagent to react with the transferred molecule or ion, whereby a presumptive color indication is produced that identifies or excludes the presence of the transferred molecule or ion as a first target molecule or ions;
    wherein the first chemical reagent comprises a micronized powder that is mixed with a dispersant to reduce the viscosity of the micronized powder to form a temporary flowable liquid applied to the solid support and thereafter dried such that the dispersant is removed.

2. The method of claim 1, wherein transferring the molecule or ion from the surface to the solid support comprises:
    rubbing the surface with a swab, whereby the molecule or ion is transferred from the surface to the swab; and
    rubbing the swab onto the solid support, whereby the molecule or ion is transferred onto the solid support.

3. The method of claim 1, further comprising
    transferring the molecule or ion from the surface to a plurality of second chemical reagents applied to the solid support; and
    allowing the second chemical reagents to react with the transferred molecule or ion, whereby a presumptive color indication is produced that identifies or excludes the presence of the transferred molecule or ion as a one or more target molecules or ions.

4. The method of claim 1, wherein the first chemical reagent comprises a micronized powder mixed with a dispersant to reduce the viscosity of the reagent powder to a temporary flowable liquid applied to the solid support.

5. The method of claim 4, wherein the dispersant is selected from the group consisting of acrylic acid, polyvinyl alcohol, amino crosslinkers, polyvinyl pyrollidinone, glycol-ethers, styrene, polyester, vinyl chloride, polyethylene, natural gums, polyether and polyamide units.

6. The method of claim 1, wherein the target molecule or ion is a dissolved hydrogen ion and the chemical reagent is selected from a group consisting of cresol red, methyl violet, crystal violet, ethyl violet, malachite green, methyl green, 2-(p-dimethylaminophenylazo)pyridine, paramethyl red, metanil yellow, 4-phenylazodiphenylamine, thymol blue, metacresol purple, orange IV, 4-o-tolylazo-o-toluidine, quinaldine red, 4,4'-bis(4-amino-1-naphthylazo)-2,2'-stilbenedisulfonic acid, p-naphtholbenzein, phenolphthalein, o-cresolphthalein, ethyl bis(2,4-dimethylphenyl)ethanoate, Thymolphthalein, alizarin yellow R, alizarin, p-(2,4-dihydroxyphenylazo)benzenesulfonic acid, sodium salt, 5,5'-indigodisulfonic acid, disodium salt, and 2,4,6-trinitrotoluene, 1,3,5-trinitrobenzene, clayton yellow.

7. The method of claim 1, wherein the target molecule or ion is an organic liquid and the chemical reagent is selected from a group consisting of merocyanine dyes, 442-N-substituted-1,4-hydropyridin-4-ylidine)ethylidene]cyclohexa-2,5-di-en-1-one, red pyrazolone dyes, azomethine dyes, indoaniline dyes, diazamerocyanine dyes, indigoid dyes 2,6-diphenyl-4-(2,4,6-triphenylpyridinium-1-yl)phenolate, 1-ethyl-4-(methoxycarbonyl)pyridinium iodide, 5-(dimethylamino)-5'-nitro-2,2'-bisthiophene, reichart's dye, (2,4,6-triphenyl-1-pyridinio)-2,6-diphenylphenolate, and 9-diethylamino-5-benzo[a]phenoxazinone.

8. The method of claim 1, wherein the target molecule or ion is reactive nitrogen and the chemical reagent is selected from a group consisting of 6-amino-1-naphthol-3-sulphonic acid, zinc, diphenylbenzidine, phenylanthranilic acid, aniline sulfate, diphenylamine, ethylenediamine, N-1 naphthyl dihydrochloride, potassium iodide, bismuth nitrate, sulfamic acid, sodium hydrogen sulphate, sulfanilamide, and hexachloroplatinic(IV) acid hydrate.

9. The method of claim 1, wherein the target molecule or ion is a reactive halogen or free radical and the chemical reagent is selected from a group consisting of ammonium thiocyanate, 2,2'-bipyridine (Ru complex), nitrophenanthroline (Fe complex), manganous sulphate, phenylanthranilic acid, 1,10-Phenanthroline iron(II) sulfate complex, indigo carmine, copper sulphate, N-ethoxychrysoidine, analine, 2,2'-Bipyridine (Fe complex), methylene blue, 5,6-dimethylphenanthroline (Fe complex), o-dianisidine, ferrous sulphate, p-amino-N,N-diethylaniline sulfate, sodium diphenylamine sulfonate, diphenylbenzidine, diphenylamine, and viologen.

* * * * *